United States Patent
Parsons et al.

(10) Patent No.: US 9,808,240 B2
(45) Date of Patent: Nov. 7, 2017

(54) RETRACTABLE CANNULATED SUTURE PASSER AND METHOD OF PASSING SUTURE

(71) Applicant: Arthrex, Inc., Naples, FL (US)

(72) Inventors: Bradford O. Parsons, Irvington, NY (US); Peter J. Dreyfuss, Naples, FL (US)

(73) Assignee: Arthrex, Inc., Naples, FL (US)

(*) Notice: Subject to any disclaimer, the term of this patent is extended or adjusted under 35 U.S.C. 154(b) by 304 days.

(21) Appl. No.: 14/594,751

(22) Filed: Jan. 12, 2015

(65) Prior Publication Data

US 2016/0199057 A1  Jul. 14, 2016

(51) Int. Cl.
*A61B 17/04* (2006.01)
*A61B 17/06* (2006.01)

(52) U.S. Cl.
CPC .... *A61B 17/0485* (2013.01); *A61B 2017/061* (2013.01); *A61B 2017/0608* (2013.01)

(58) Field of Classification Search
CPC .......... A61B 17/0485; A61B 2017/061; A61B 2017/0608
USPC ......... 606/139, 144, 148, 232; 600/104, 115
See application file for complete search history.

(56) References Cited

U.S. PATENT DOCUMENTS

| | | | |
|---|---|---|---|
| 7,842,050 B2 | 11/2010 | Diduch et al. | |
| 7,998,148 B2 * | 8/2011 | Pasricha | A61B 1/0014 606/139 |

OTHER PUBLICATIONS

"Arthrex Suture Lasso", http://www.arthrex.com/shoulder/suturelassos-category#suturelassos-category/products/?types=all&locales=en&taxonomy=suturelassos_category&time-0&sort=datedesc, Arthrex 2013.

* cited by examiner

*Primary Examiner* — Vy Bui
(74) *Attorney, Agent, or Firm* — Rubin & Rudman LLP

(57) ABSTRACT

A suture passer and method for passing suture in tissue repair and other surgical procedures. The suture passer has an outer stiff tube component and a flexible tube component which is both cannulated and retractable. The inner tube (i.e., the cannulated, flexible, retractable tube) is preferably made of NiTi and has a predefined curve. The inner tube is deployed and retracted from the outer stiff tube. The configuration of the inner tube allows the instrument to be introduced into a space through a small portal and then deployed to provide leverage and improved reach (without creating large portals).

11 Claims, 2 Drawing Sheets

RETRACTABLE CANNULATED SUTURE PASSER AND METHOD OF PASSING SUTURE

FIELD OF THE INVENTION

The present invention relates to a surgical instrument for suturing tissue and, more particularly, to a retractable cannulated suture passer used to pass suture through tissue.

BACKGROUND OF THE INVENTION

Surgical procedures require time-consuming suturing of soft tissue. Generally, suture needles with attached suture strands are grasped either manually or by forceps and passed through the desired work site so a knot can be tied. In endoscopic procedures, where access to the work site is inherently limited, surgeons must use auxiliary devices to be able to pass suture strands through desired tissue.

Various instruments and techniques have been developed for surgical repairs requiring the passing of sutures to otherwise difficult to access locations. For example, the "Lasso" type devices such as Arthrex SutureLasso™ for hip arthroscopy has an extended and reinforced shaft that makes it the preferred option for suture shuttling during labral repair and capsular closure procedures by reaching into the deep recesses of the hip joint. Similarly, the Micro SutureLasso™ provides 20-gauge needles for arthroscopic suture passing in upper and lower extremities. The ergonomic plastic handle of the suture passer facilitates accurate placement and control. Advancement of a pre-loaded fine nitinol wire loop shuttles any suture through tissue. A selection of straight and curved shafts provides accessibility to difficult to reach structures.

While suitable for accessing difficult to reach areas and structures, these devices require, however, large portals to accommodate the instruments, particularly at work sites that are too small to accommodate such instruments. These devices are also fixed and rigid and, thus, could not conform to the curved anatomy of some of the internal structures.

Accordingly, there is a need for an improved suture passing instrument that overcomes the disadvantages of the prior art and allows a surgeon to quickly, accurately, and easily pass suture through soft tissue, without requiring the need for large portals at the surgical site to accommodate such suture passing instruments. Also needed are methods of passing a flexible strand such as suture at difficult-to-reach locations and with improved leverage and reach.

SUMMARY OF THE INVENTION

The present invention provides a suture passing instrument and technique for surgical repairs. The novel suture passer has an outer stiff tube component and a flexible inner tube component which is both cannulated and retractable. The inner tube (i.e., the cannulated, flexible, retractable tube) is preferably made of NiTi and has a predefined curve. The inner tube is deployed and retracted from the outer stiff tube. The configuration of the inner tube allows the instrument to be introduced into a space through a small portal and then deployed to provide leverage and improved reach (without creating large portals).

These and other features and advantages of the invention will become apparent from the following detailed description when read in conjunction with the accompanying drawings and illustrated exemplary embodiments of the invention.

DESCRIPTION OF THE INVENTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

The present invention provides a suture passing instrument and surgical techniques for endoscopic surgical repairs, for example, arthroscopic surgeries. The suture passer has an outer stiff tube component that houses a flexible tube component which is both cannulated and retractable. The inner tube (i.e., the cannulated, flexible, retractable tube) is preferably made of NiTi and has a predefined curve. The inner tube is deployed and retracted from the outer stiff tube. The configuration of the inner tube allows the instrument to be introduced into a space through a small portal and then deployed to provide leverage and improved reach (without creating large portals).

Figure 1:
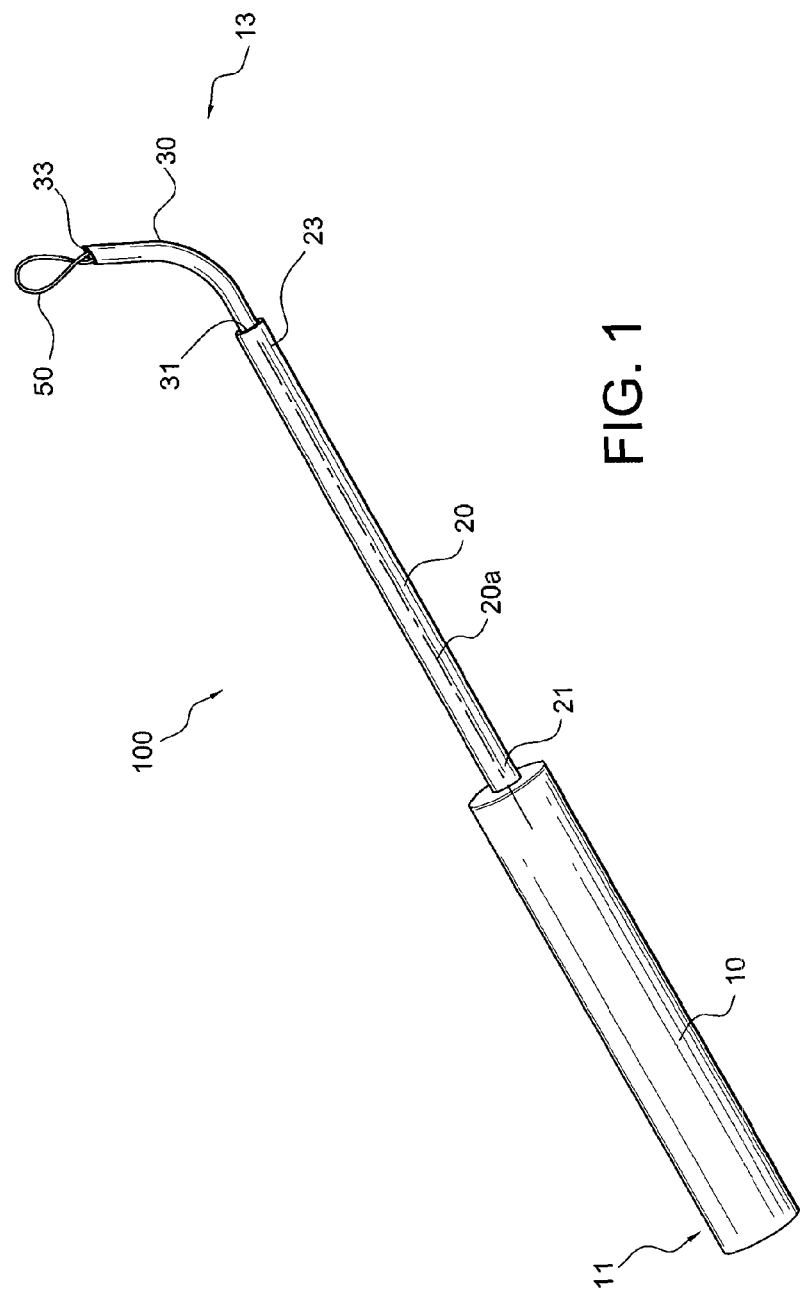
FIG. 1 is a perspective view of a suture passing instrument according to an embodiment of the present invention.
Figure 3:
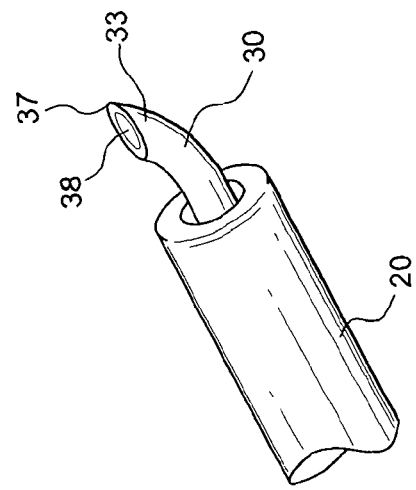
FIG. 3 is an enlarged view of the suture passing instrument of the present invention (showing the flexible tube component in the retracted state).
Figure 2:
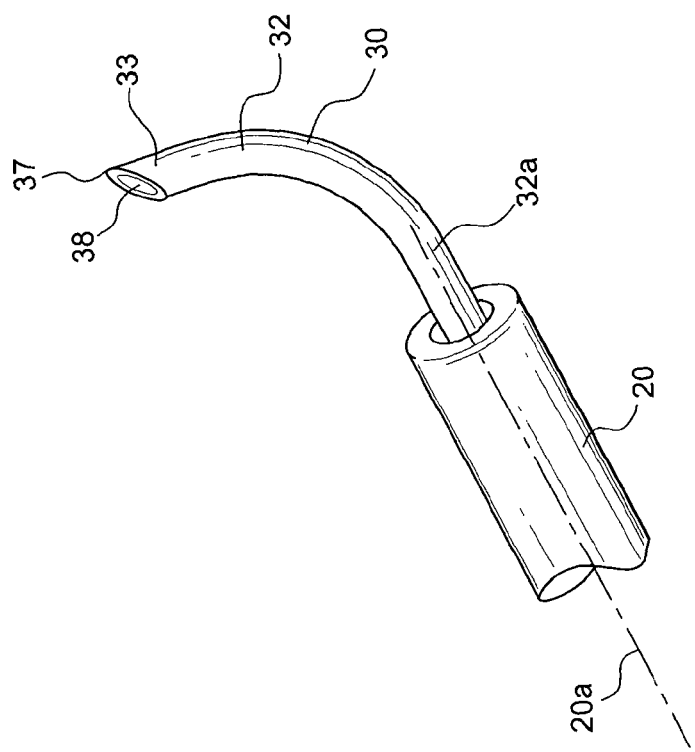
FIG. 2 is an enlarged view of the distal end of the suture passing instrument of FIG. 1 (showing the flexible tube component in the deployed state).

Referring now to the drawings, where like elements are designated by like reference numerals, FIGS. 1-3 illustrate various structural elements of suture passing instrument 100 (suture passer 100) of the present invention provided with a rigid outer elongated tube 20 designed to house a flexible inner tube 30 that receives a shuttling device or suture capturing member 50, for example, a Nitinol loop that is used to capture and pass suture (flexible strand) through tissue.

FIG. 1 illustrates suture passing instrument 100 of the present invention comprising a handle 10, an elongated tubular member or shaft 20 and an inner flexible member 30. Elongated tubular member 20 has a longitudinal axis 20a, a proximal end 21, a distal end 23 and an axial throughbore therein (not shown). Elongated tubular member 20 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity. Elongated tubular member 20 is formed of a rigid, stiff material such as stainless steel or any rigid, medically acceptable metal or plastic material that does not allow bending or flexing.

Elongated tubular member 20 connects to handle 10 at the proximal end 21 and is preferably integral with the handle 10. As illustrated in FIG. 1, the rigid tubular member 20 is substantially straight with respect to the handle 10 and is fully cannulated to allow the inner flexible member with shuttling device 50 to pass therethrough and to capture and retain at least one flexible strand, for example, suture.

Inner flexible member 30 is provided in the form of a flexible tube component that has an outer diameter smaller than the inner diameter of the axial throughbore of the elongated tubular member 20, to allow the inner flexible member to be easily manipulated within the outer tubular member. Preferably, the inner flexible member 30 is provided in the form of a cannulated, flexible, retractable tube that is made of NiTi or similar materials and/or alloys. The inner flexible member has a predefined curve. The curve may be for example, 25°, 30°, 45°, 90° or have a crescent configuration. As shown in FIG. 2, in the deployed position/state, region 32 of the inner flexible member 30 has a substantially curved configuration in that about 80% to 100% of its length is curved, while region 32*a* is a substantially linear region. Distal end 33 of the inner flexible member 30 is configured to engage and retrieve at least one flexible strand (for example, suture).

As more clearly shown in FIGS. 2 and 3, the distal end 33 of the inner flexible member 30 is provided with a sharp needle tip 37 having an opening 38 that allows the shuttling device 50 (suture capturing mechanism 50) shown in FIG. 1, for example, a wire loop in the form of a braided Nitinol loop 50, to be pushed through the surgical instrument 100 and to extend out the sharp needle tip 37 of the inner flexible member of the instrument, as shown in FIG. 1. Since the braided Nitinol loop 50 must pass through the instrument 100 without any interference, the edges of the opening 38 must not abrade the Nitinol loop 50 or the suture to be subsequently retrieved. Accordingly, the edges of the opening 38 are preferably beveled.

The inner tube 30 is deployed and retracted from the outer stiff tube 20. FIG. 2 illustrates the inner tube in the deployed or expanded/extended or non-retracted configuration. FIG. 3 illustrates the inner tube in the retracted or undeployed configuration. The configuration of the inner tube allows the instrument 100 to be introduced into a space through a small portal and then deployed to provide leverage and improved reach (without creating large portals).

Handle 10 of the suturing instrument 100 (illustrated in FIG. 1) is provided at the proximal end 11 of the instrument and may include various mechanisms and/or actuators for manipulating the inner tube 30 relative to the outer stiff tube 20. For example, handle 10 may be provided with a trigger or actuating mechanism which may be pivotally connected to the handle. The trigger mechanism may consist of a finger lever which, when actuated, is designed to move the inner tube relative to the outer tube. Similar to the handles of the SutureLassos™-type devices, the handle 10 could be also provided with a thumb pad used for easy, one-handed wire advancement.

The surgical instrument 100 of the present invention described above with reference to FIGS. 1-3 may be employed in various surgical medical procedures for retrieving, transferring, treating, closing and/or tightening sutures and suture loops during surgical procedures. For example, the suture retrieving instrument 100 may be employed in endoscopic and arthroscopic procedures, including but not limited to arthroscopic rotator cuff repair, Bankhart shoulder repair, meniscal repair, and any orthopaedic procedure that requires manipulation of suture through soft tissue or bone tunnels, for example, or in conjunction with fixation devices, such as suture anchors. Additionally, the instrument 100 may be utilized in other general surgical and specialty procedures that require suturing at a remote site, such as inside the body. The instrument of the present invention may be also used in repairs where suture visibility or finger access can be limited. As a result of its curved configuration, the suture passer/retriever instrument 100 of the invention has particular applicability to rotator cuff repair procedures, during which the instrument can be easily passed through the Neviaser Portal while the patient is positioned in the Beach Position.

It will be appreciated, of course, that while the surgical instrument 100 may be particularly useful for performing remote procedures through access sheaths, cannulas and trocars, it will also find use in open surgical procedures where its ability to capture suture will also provide advantages.

The surgical instrument 100 of the present invention may also be used without the Nitinol loop 50, as a suture passing instrument. For example, a stiff suture such as FiberStick™ sold by the assignee of the present application, Arthrex, Inc., may be inserted through the cannulated shaft 20, 30 of the surgical instrument 100 and after piercing of the tissue with sharp needle tip 37 of the instrument. The end of the FiberStick™ suture that has been passed through the tissue may then be retrieved and used to tie down the tissue.

In an exemplary embodiment only, suture passing instrument 100 may have the configuration and dimensions of a Small Diameter SutureLasso™ (SutureLasso™ SD) but would differ in that instrument 100 is provided with retractable, cannulated inner tube 30 that allows a flexible strand, for example, Nitinol wire shuttle loop or a FiberStick™, to be pre-loaded therein and aid in suture passing and manipulating.

In use, instrument 100 is pre-loaded with the shuttling device 50 (suture capturing mechanism 50) which may be a Nitinol wire shuttle loop, or a monofilament suture loop, or a snare made of Nitinol wire, or a FiberStick™ (for example, a #2 FiberWire® with 12 inches stiffened portion which may be used with a PushLock® anchor). The instrument 100 is inserted into the tissue to be sutured, the inner flexible member 30 is deployed to allow shuttling device 50 to capture and secure a flexible strand (an end of a suture) and then the end of suture is shuttled through the tissue and retrieved out of an accessory portal without removing the instrument from the surgical site. The instrument is then reinserted through the tissue, adjacent the first stitch (for example, parallel to the first stitch) and the shuttling device 50 is then retrieved out of a cannula, another end of the suture is placed within the shuttling device and then create a mattress stitch.

The suture passing instrument 100 has particular application to arthroscopic Bankart, SLAP and rotator cuff repairs. The instrument 100 may have a 1.25 mm, 1.8 mm or 2.3 mm outer diameter tip. The 1.25 mm device may be employed for percutaneous suture passing for rotator cuff repairs and glenoid labrum repairs. As noted above, the instrument 100 may be provided pre-loaded with a Nitinol loop or similar device to accomplish a simple shuttle step to pass suture through tissue. The instrument is a reliable device for providing multiple suture passes without failure. The instrument 100 may be also employed as a transosseous suture passer, for passing grafts or suture through bony sockets and tunnels (with a 6-inch working length).

In an exemplary and illustrative embodiment only, a method of suturing tissue using the suture passing instrument 100 of the present invention comprises the steps of: (i) providing a suture passing instrument 100 in the proximity of anatomical tissue to be sutured, the suture passing instrument comprising an outer stiff tubular member and an inner, retractable cannulated member; (ii) deploying the inner member so that the inner member extends away from a most distal end of the stiff outer member and in a direction non-parallel to a longitudinal axis of the outer stiff tubular member; (iii) capturing a flexible strand (suture) with the inner member; and (iv) retracting the inner member within the outer member to advance/shuttle the flexible strand through tissue to be sutured.

According to another exemplary and illustrative embodiment only, a method of suturing a tissue using the suture passing instrument 100 of the present invention comprises the steps of: (i) providing a suture passer instrument pre-loaded with a shuttling device (a suture capturing member), the suture passer instrument comprising a cannulated handle, a shaft (cannulated stiff tube component) that houses a cannulated inner flexible component, the shuttling device (suture capturing member) extending through the cannulated handle, the cannulated inner flexible component and the cannulated stiff tube component (shaft), wherein the cannulation of the shaft is sized to allow the suture capturing member to pass therethrough and to retain suture; (ii) positioning the suture passer instrument in the proximity of tissue to be sutured at a surgical site; (iii) deploying the inner member out of the outer stiff component; (iv) capturing suture with the suture capturing member; and (v) retracting the inner member to allow the captured suture to pass through the tissue to be sutured.

According to exemplary embodiments only, the suture passing instrument 100 of the present invention may be employed for passing sutures side-to-side to appose two separate leaves of soft tissue (e.g., tendon), or to pass suture from a suture anchor through soft tissue to appose soft tissue (e.g., tendon) to bone.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A suture passing instrument comprising:
   a cannulated outer tube having a longitudinal axis, a distal end and a proximal end;
   an inner flexible cannulated tube housed within the cannulated outer tube, the inner flexible cannulated tube being adapted to deploy and retract relative to the cannulated outer tube, the inner flexible cannulated tube having a substantially curved region at its distal end, the distal end of the inner flexible cannulated tube being provided with a sharp needle tip having an opening that allows a shuttling device or suture capturing member to be pushed through the suture passing instrument and to extend out the sharp needle tip of the inner flexible cannulated tube; and
   a cannulated handle coupled to the cannulated outer tube.

2. The suture passing instrument of claim 1, wherein the inner flexible cannulated tube is sized to allow the suture capturing member to pass therethrough and to retain suture.

3. The suture passing instrument of claim 2, wherein the suture capturing member is a wire loop, a snare or a FiberStick™ strand.

4. The suture passing instrument of claim 3, wherein the suture capturing member is a Nitinol wire loop.

5. The suture passing instrument of claim 1, wherein the inner flexible cannulated tube is formed of NiTi.

6. The suture passing instrument of claim 1, wherein the cannulated outer tube is formed of stainless steel or similar metal.

7. The suture passing instrument of claim 1, wherein the inner flexible tube is at least partially housed within the cannulated outer tube.

8. A method of suturing tissue with a suture passer, the method comprising the steps of:
   pre-loading a suture passer with a suture capturing member, the suture passer comprising a cannulated shaft having a proximal end and a distal end, and a handle attached to the proximal end of the cannulated shaft, wherein the cannulated shaft consists of a rigid outer tube and a flexible inner tube housed within the rigid outer tube, the flexible inner tube being configured to deploy and to retract relative to the rigid outer tube;
   positioning the suture passer in the vicinity of tissue to be sutured at a surgical site;
   advancing the suture passer through the tissue to be sutured;
   deploying the flexible inner tube so that the flexible inner tube extends away from a most distal end of the rigid outer tube and in a direction non-parallel to a longitudinal axis of the rigid outer tube;
   capturing a flexible strand within a loop of the suture capturing member passing through the cannulated shaft and the handle; and
   withdrawing the captured flexible strand from the surgical site.

9. The method of claim 8, wherein the loop is part of a Nitinol wire loop.

10. The method of claim 8, wherein the flexible inner tube is formed of NiTi.

11. The method of claim 8, wherein the rigid outer tube is formed of stainless steel.

* * * * *